US00PP24958P2

(12) United States Plant Patent
Barends

(10) Patent No.: US PP24,958 P2
(45) Date of Patent: Oct. 7, 2014

(54) ***PELARGONIUM* PLANT NAMED 'FIPELMASBRIREDIMP'**

(50) Latin Name: *Pelargonium×hortorum*
Varietal Denomination: Fipelmasbriredimp

(71) Applicant: Eveline Barends, De Lier (NL)

(72) Inventor: Eveline Barends, De Lier (NL)

(73) Assignee: Fides B.V., De Lier (NL)

( * ) Notice: Subject to any disclaimer, the term of this patent is extended or adjusted under 35 U.S.C. 154(b) by 67 days.

(21) Appl. No.: 13/694,557

(22) Filed: Dec. 12, 2012

(51) Int. Cl.
*A01H 5/00* (2006.01)

(52) U.S. Cl.
USPC ..... Plt./330

(58) Field of Classification Search
USPC ..... Plt./330
See application file for complete search history.

*Primary Examiner* — Kent L Bell
(74) *Attorney, Agent, or Firm* — C. A. Whealy

(57) ABSTRACT

A new and distinct cultivar of *Pelargonium* plant named 'Fipelmasbriredimp', characterized by its upright and outwardly spreading growth habit; rounded plant habit; vigorous growth habit; medium green-colored leaves with distinct zonation pattern; early and freely flowering habit; large semi-double bright red-colored flowers held above and beyond the foliar plane on strong peduncles; and good garden performance.

1 Drawing Sheet

Botanical designation: *Pelargonium×hortorum*.
Cultivar denomination: 'FIPELMASBRIREDIMP'.

BACKGROUND OF THE INVENTION

The present invention relates to a new and distinct cultivar of *Pelargonium* plant, botanically known as *Pelargonium×hortorum*, commercially referred to as Zonal Geranium and hereinafter referred to by the name 'Fipelmasbriredimp'.

The new *Pelargonium* plant is a product of a planned breeding program conducted by the Inventor in De Lier, The Netherlands. The objective of the breeding program is to create new compact and freely-flowering *Pelargonium* plants that flower early and have attractive leaf and flower coloration.

The new *Pelargonium* plant originated from a cross-pollination made by the Inventor in September, 2006 in De Lier, The Netherlands of a proprietary selection of *Pelargonium×hortorum* identified as code number 60008, not patented, as the female, or seed, parent with a proprietary selection of *Pelargonium×hortorum* identified as code number 88875, not patented, as the male, or pollen, parent. The new *Pelargonium* plant was discovered and selected by the Inventor as a single flowering plant from within the progeny of the stated cross-pollination in a controlled greenhouse environment in De Lier, The Netherlands, in March, 2007.

Asexual reproduction of the new *Pelargonium* plant by vegetative terminal cuttings in a controlled greenhouse environment in De Lier, The Netherlands, since July, 2007 has shown that the unique features of this new *Pelargonium* plant are stable and reproduced true to type in successive generations.

SUMMARY OF THE INVENTION

Plants of the new *Pelargonium* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Fipelmasbriredimp'. These characteristics in combination distinguish 'Fipelmasbriredimp' as a new and distinct *Pelargonium* plant:

1. Upright and outwardly spreading growth habit; rounded plant habit.
2. Vigorous growth habit.
3. Medium green-colored leaves with distinct zonation pattern.
4. Early and freely flowering habit.
5. Large semi-double bright red-colored flowers held above and beyond the foliar plane on strong peduncles.
6. Good garden performance.

Plants of the new *Pelargonium* differ primarily from plants of the parent selections in plant habit as plants of the new *Pelargonium* are more uniform than plants of the parent selections.

Plants of the new *Pelargonium* can be compared to plants of *Pelargonium×hortorum* 'Fipelmasred', disclosed in U.S. Plant Pat. No. 22,735. In side-by-side comparisons conducted in De Lier, The Netherlands, plants of the new *Pelargonium* differed primarily from plants of 'Fipelmasred' in growth habit as plants of the new *Pelargonium* were more vigorous than plants of 'Fipelmasred'. In addition, plants of the new *Pelargonium* had slightly lighter red-colored flowers than plants of 'Fipelmasred'.

BRIEF DESCRIPTION OF THE PHOTOGRAPH

The accompanying colored photograph illustrates the overall appearance of the new *Pelargonium* plant showing the colors as true as it is reasonably possible to obtain in colored reproductions of this type. Colors in the photograph may differ slightly from the color values cited in the detailed botanical description which accurately describe the colors of the new *Pelargonium* plant. The photograph comprises a side perspective view of typical flowering plants of 'Fipelmasbriredimp' grown in a container.

DETAILED BOTANICAL DESCRIPTION

The aforementioned photograph and following observations, measurements and values describe plants grown during the summer in 15-cm containers in a glass-covered greenhouse in De Lier, The Netherlands and under cultural practices typical of commercial *Pelargonium* production. During the production of the plants, day temperatures ranged from 16° C. to 28° C. and night temperatures ranged from 14° C. to 18° C. Plants were ten weeks old when the photograph and the description were taken. In the detailed description, color references are made to The Royal Horticultural Society Colour Chart, Fifth Edition, except where general terms of ordinary dictionary significance are used.

Botanical classification:

*Pelargonium×hortorum*.—'Fipelmasbriredimp'.

Parentage:

*Female, or seed, parent*.—Proprietary selection of *Pelargonium×hortorum* identified as code number 60008, not patented

*Male or pollen parent*.—Proprietary selection of *Pelargonium×hortorum* identified as code number 88875, not patented.

Propagation:

*Type*.—By vegetative terminal cuttings.

*Time to initiate roots, summer*.—About four days at temperatures of 22° C.

*Time to initiate roots, winter*.—About seven days at temperatures of 22° C.

*Time to produce a rooted young plant, summer*.—About 16 days at temperatures of 22° C. to 30° C.

*Time to produce a rooted young plant, winter*.—About 21 days at temperatures of 20° C. to 25° C.

*Root description*.—Medium in thickness, fibrous; greyed white in color.

*Rooting habit*.—Moderately freely branching, medium density.

Plant description:

*Plant form and growth habit*.—Upright and outwardly spreading growth habit; rounded and uniformly mounded plant habit; densely foliated; about five basal branches developing per plant; moderate growth rate; vigorous growth habit.

*Plant height, to top of umbels*.—About 44 cm.

*Plant height, to top of foliar plane*.—About 26 cm.

*Plant width*.—About 32 cm.

*Lateral branches*.—Length: About 4 cm to 17 cm. Diameter: About 5 mm to 7 mm. Internode length: About 1 cm to 3 cm. Texture: Pubescent. Strength: Moderately strong. Color: Close to 144A.

Foliage description:

*Arrangement*.—Alternate; simple.

*Length*.—About 5 cm to 7 cm.

*Width*.—About 8.5 cm to 12 cm.

*Shape*.—Reniform.

*Apex*.—Obtuse.

*Base*.—Cordate.

*Margin*.—Crenate.

*Venation pattern*.—Palmate.

*Texture, upper surface*.—Smooth, glabrous.

*Texture, lower surface*.—Slightly pubescent; pubescence more dense along venation.

*Color*.—Developing leaves, upper surface: Close to 137C. Developing leaves, lower surface: Close to 147B. Fully expanded leaves, upper surface: Close to 137B; venation, close to N137A. Fully expanded leaves, lower surface: Close to 147B; venation, close to 146C. Zonation pattern: Location: Center of the leaf. Width: About 2.5 cm. Color: Close to 178A slightly tinged with green.

*Petiole*.—Length: About 8 cm. Diameter: About 2 mm to 3 mm. Texture, upper and lower surfaces: Pubescent. Color, upper and lower surfaces: Close to 146A.

Flower description:

*Flower arrangement*.—Semi-double rotate flowers arranged in rounded hemispherical umbels arising from apical leaf axils; umbels displayed above the foliage on strong peduncles; flowers face upright to outwardly depending on position on the umbel.

*Fragrance*.—None detected.

*Quantity of flowers*.—Freely flowering habit; about 37 to 42 flowers developing per umbel and about nine to eleven umbels developing per plant.

*Flowering season*.—In The Netherlands, flowering is continuous from late spring until frost in the autumn; early flowering habit, plants begin flowering about eight to ten weeks after planting.

*Flower longevity*.—Depending on environmental conditions, individual flowers last about 2 to 14 days on the plant; flowers persistent.

*Umbel height*.—About 5 cm.

*Umbel diameter*.—About 9 cm.

*Flower diameter*.—About 4.5 cm by 4.8 cm.

*Flower depth (height)*.—About 8 mm.

*Flower buds, prior to anthesis*.—Length: About 1.4 cm. Diameter: About 8 mm. Shape: Globular to elliptical. Color: Close to 44B.

*Petals*.—Quantity per flower: About seven to nine. Length: About 2.5 cm. Width: About 2.2 cm. Shape: Spatulate to obovate. Apex: Obtuse. Base: Attenuate. Margin: Entire. Texture, upper and lower surfaces: Smooth, glabrous; velvety. Color: When opening and fully opened, upper surface: Close to 44A; color does not fade with development. When opening and fully opened, lower surface: Close to 43B; color does not fade with development.

*Petaloids*.—Quantity per flower: About one or two. Length: About 1 cm to 2 cm. Width: About 2 mm to 10 mm. Shape: Roughly obovate to oblanceolate. Apex: Roughly obtuse. Base: Attenuate. Margin: Entire. Texture, upper and lower surfaces: Smooth, glabrous; velvety. Color: When opening and fully opened, upper surface: Close to 44A; color does not fade with development. When opening and fully opened, lower surface: Close to 43B; color does not fade with development.

*Sepals*.—Quantity per flower: Five arranged in a single whorl. Length: About 1 cm. Width: About 3 mm. Shape: Lanceolate/ovate to acicular. Apex: Acute. Base: Lobate to truncate. Margin: Entire. Texture, upper and lower surfaces: Densely pubescent. Color, upper surface: Close to 146B; towards the base, close to 60B. Color, lower surface: Close to 146B; towards the margins, close to 60B.

*Peduncle (umbel stem)*.—Length: About 16 cm to 18 cm. Diameter: About 4 mm. Strength: Strong. Angle:

Erect to about 30° C. from vertical. Texture: Pubescent. Color: Close to 146B.

*Pedicel* (*individual flower stem*).—Length: About 2.5 cm to 2.7 cm. Diameter: About 1 mm. Strength: Moderately strong. Angle: Erect to about 60° C. from vertical. Texture: Pubescent. Color: Close to 178A.

*Reproductive organs*.—Androecium: Stamen quantity per flower: About six to eight. Filament length: About 2 mm to 5 mm. Filament color: Close to 155D. Anther length: About 2 mm to 3 mm. Anther shape: Oblong. Anther color: Close to 39A. Pollen amount: Moderate. Pollen color: Close to 33B. Gynoecium: Pistil quantity per flower: One. Pistil length: About 1 cm. Stigma shape: Tapering; reflexed. Stigma color: Close to 60A. Style length: About 8 mm. Style color: Close to N144B. Ovary color: Close to 146C.

*Fruits and seeds*.—Fruit and seed development have not been observed on plants of the new *Pelargonium*.

Disease & pest resistance: Plants of the new *Pelargonium* have not been observed to be resistant to pathogens and pests common to *Pelargoniums*.

Garden performance: Plants of the new *Pelargonium* have been observed to tolerate rain, wind, and temperatures ranging from about 1° C. to about 45° C. and have demonstrated good garden performance.

It is claimed:

1. A new and distinct *Pelargonium* plant named 'Fipelmasbriredimp' as illustrated and described.

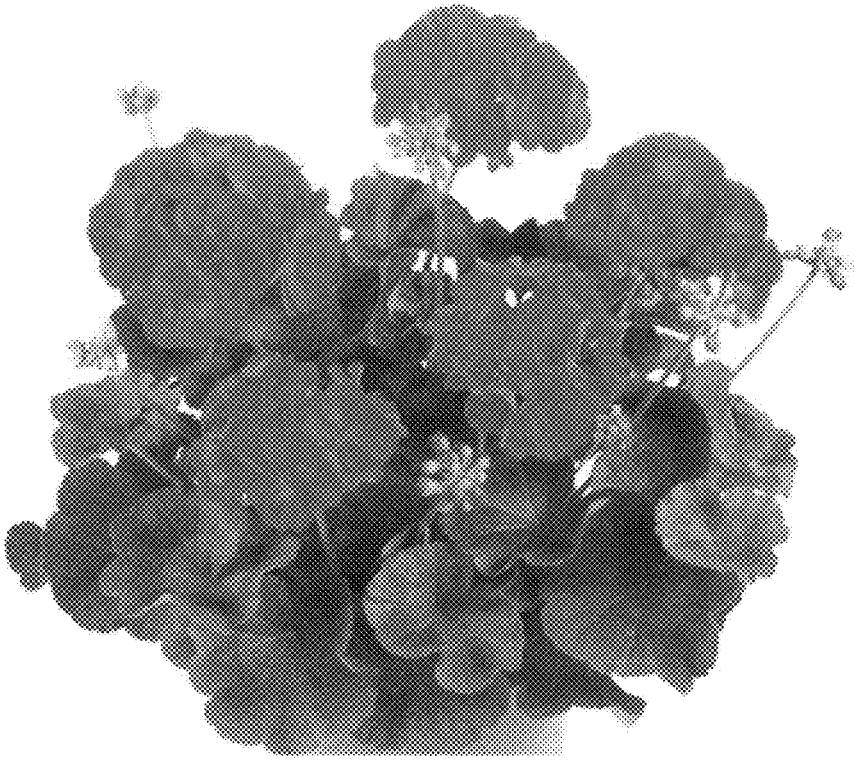

* * * * *